US011072784B2

(12) United States Patent
Tournier et al.

(10) Patent No.: US 11,072,784 B2
(45) Date of Patent: *Jul. 27, 2021

(54) ESTERASES AND USES THEREOF

(71) Applicant: CARBIOS, Saint-Beauzire (FR)

(72) Inventors: Vincent Tournier, Toulouse (FR); Hélène Texier, Eaunes (FR); Marie-Laure Desrousseaux, Lompret (FR); Christopher Topham, Lavaur (FR); Isabelle Andre, Toulouse (FR); Sophie Barbe, Goyrans (FR); Sophie Duquesne, Toulouse (FR); Alain Marty, Toulouse (FR)

(73) Assignee: CARBIOS, Saint-Beauzire (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/819,222

(22) Filed: Mar. 16, 2020

(65) Prior Publication Data

US 2020/0277585 A1 Sep. 3, 2020

Related U.S. Application Data

(63) Continuation of application No. 16/317,178, filed as application No. PCT/EP2017/067577 on Jul. 12, 2017, now Pat. No. 10,590,401.

(30) Foreign Application Priority Data

Jul. 12, 2016 (EP) .................................... 16305899

(51) Int. Cl.
*C12N 9/18* (2006.01)
*C12N 15/52* (2006.01)

(52) U.S. Cl.
CPC ............... *C12N 9/18* (2013.01); *C12N 15/52* (2013.01); *C12Y 301/01074* (2013.01); *C12Y 301/01001* (2013.01)

(58) Field of Classification Search
CPC .................................. C12N 9/18; C12N 15/52
See application file for complete search history.

(56) References Cited

U.S. PATENT DOCUMENTS

| | | |
|---|---|---|
| 9,476,073 B2 | 10/2016 | Boisart |
| 9,528,132 B2 | 12/2016 | Mazzoli et al. |
| 10,124,512 B2 | 11/2018 | Boisart et al. |
| 10,287,561 B2 | 5/2019 | Alvarez et al. |
| 10,385,183 B2 | 8/2019 | Maille |
| 10,584,329 B2 * | 3/2020 | Dykes ..................... C12Q 1/04 |
| 10,590,401 B2 * | 3/2020 | Tournier ................. C12N 9/18 |
| 2015/0056673 A1 | 2/2015 | Boisart |
| 2015/0167030 A1 | 6/2015 | Mazzoli et al. |
| 2015/0290840 A1 | 10/2015 | Boisart et al. |
| 2016/0280881 A1 | 9/2016 | Boisart et al. |
| 2017/0114205 A1 | 4/2017 | Maille |
| 2017/0313998 A1 | 11/2017 | Alvarez et al. |
| 2017/0349723 A1 | 12/2017 | Ferreira et al. |
| 2018/0051264 A1 | 2/2018 | Li et al. |
| 2018/0142097 A1 | 5/2018 | Guemard et al. |
| 2018/0186943 A1 | 7/2018 | Chateau |
| 2019/0002933 A1 | 1/2019 | Dusseaux et al. |
| 2019/0218360 A1 | 7/2019 | Desrousseaux et al. |
| 2019/0233803 A1 | 8/2019 | Topham et al. |
| 2019/0345472 A1 | 11/2019 | Marty et al. |

FOREIGN PATENT DOCUMENTS

| | | |
|---|---|---|
| WO | WO 2012/0099018 | 7/2012 |
| WO | WO 2016/062695 | 4/2016 |
| WO | WO 2018/011284 | 1/2018 |

OTHER PUBLICATIONS

Sulaiman, S. et al. "Isolation of a Novel Cutinase Homolog with Polyethylene Terephthalate-Degrading Activity from Leaf-Branch Compost by Using a Metagenomic Approach" *Applied and Environmental Microbiology*, Mar. 2012, pp. 1556-1562, vol. 78, No. 5.
Database GenSeq [Online] Accession No. AZY25618, Sep. 13, 2012, p. 1.
Van Gemeren, I. A. et al. "Expression and Secretion of Defined Cutinase Variants by *Aspergillus awamon*" *Applied and Environmental Microbiology*, Aug. 1998, pp. 2794-2799, vol. 64, No. 8.
Database GenSeq [Online] Accession No. BCB68324, Aug. 27, 2015, p. 1, XP-002773688.
Written Opinion in International Application No. PCT/EP2017/067577, dated Sep. 26, 2017, p. 1-7.
Claims pending in U.S. Appl. No. 16/470,295, filed Jun. 17, 2019, pp. 1-4.

* cited by examiner

*Primary Examiner* — Tekchand Saidha
(74) *Attorney, Agent, or Firm* — Saliwanchik, Lloyd & Eisenschenk

(57) ABSTRACT

The present invention relates to novel esterase, more particularly to esterase variants having improved activity compared to the esterase of SEQ ID No 1 and the uses thereof for degrading polyester containing material, such as plastic products. The esterases of the invention are particularly suited to degrade polyethylene terephthalate, and material containing polyethylene terephthalate.

19 Claims, No Drawings

Specification includes a Sequence Listing.

ESTERASES AND USES THEREOF

CROSS-REFERENCE TO RELATED APPLICATIONS

This application is a continuation of U.S. application Ser. No. 16/317,178, filed Jan. 11, 2019, now U.S. Pat. No. 10,590,401, which is the U.S. national stage application of International Patent Application No. PCT/EP2017/067577, filed Jul. 12, 2017.

The Sequence Listing for this application is labeled "Seq-List.txt" which was created on Jan. 3, 2019 and is 3 KB. The entire content of the sequence listing is incorporated herein by reference in its entirety.

The present invention relates to novel esterases, more particularly to esterases having improved activity compared to a parent esterase and the uses thereof for degrading polyester containing material, such as plastic products. The esterases of the invention are particularly suited to degrade polyethylene terephthalate, and material containing polyethylene terephthalate.

BACKGROUND

Esterases are able to catalyze the hydrolysis of a variety of polymers, including polyesters. In this context, esterases have shown promising effects in a number of industrial applications, including as detergents for dishwashing and laundry applications, as degrading enzymes for processing biomass and food, as biocatalysts in detoxification of environmental pollutants or for the treatment of polyester fabrics in the textile industry. In the same way, the use of esterases as degrading enzymes for hydrolyzing polyethylene terephthalate (PET) is of particular interest. Indeed, PET is used in a large number of technical fields, such as in the manufacture of clothes, carpets, or in the form of a thermoset resin for the manufacture of packaging or automobile plastics or other parts, and PET accumulation in landfills becomes an increasing ecological problem.

Among esterases, cutinases, also known as cutin hydrolases (EC 3.1.1.74), are of particular interest. Cutinases have been identified from various fungi (P. E. Kolattukudy in "Lipases", Ed. B. Borg-ström and H. L. Brockman, Elsevier 1984, 471-504), bacteria and plant pollen. Recently, metagenomics approaches have led to identification of additional esterases.

The enzymatic degradation is considered as an interesting solution to decrease such plastic waste accumulation. Indeed, enzymes may accelerate hydrolysis of polyester containing material, and more particularly of plastic products, even up to the monomer level. Furthermore, the hydrolysate (i.e., monomers and oligomers) can be recycled as material for synthesizing new polymers.

In this context, several esterases have been identified as candidate degrading enzymes. For instance, several variants of the esterase of *Fusarium solani pisi* have been published (Appl. Environm. Microbiol. 64, 2794-2799, 1998; Proteins: Structure, Function and Genetics 26, 442-458, 1996).

However, there is still a need for esterases with improved activity to allow a process with higher efficiency and thereby to enhance the competitiveness of biological polyester degrading process.

SUMMARY OF THE INVENTION

The present invention provides new variants of esterase exhibiting increased activity compared to a parent, or wild-type esterase. These esterases are particularly useful in processes for degrading plastic material and product, such as plastic material and product containing PET. More particularly, the present invention provides variants of an esterase having the amino acid sequence as set forth in SEQ ID No 1, that corresponds to the amino acids 36 to 293 of the amino acid sequence of the metagenome-derived cutinase described in Sulaiman et al., Appl Environ Microbiol. 2012 March, or to the amino acids 36 to 293 of the amino acid sequence referenced G9BY57 in SwissProt.

In this regard, it is an object of the invention to provide an esterase variant which (i) has at least 75%, 80%, 85%, 90%, 95% or 99% identity to the full length amino acid sequence set forth in SEQ ID No 1, and (ii) has at least one substitution at a position selected from F208, T157, T176, S65, G53, A121, V170, S223, P58, A62, A64, L67, A68, N85, T86, R89, D91, P93, R96, G128, M131, G133, G134, L152, T153, P154, H156, A178, P179, H183, S206, A209, P210 or N211, wherein the positions are numbered by reference to the amino acid sequence set forth in SEQ ID No 1, and (iii) exhibits increased polyester degrading activity compared to an esterase of SEQ ID No 1.

More particularly, the esterase comprises at least one substitution at a position selected from F208, T157, T176, G53, A121, V170, S65, or N211.

According to a particular embodiment, the esterase comprises at least one substitution or combination of substitutions selected from the group consisting of G53L, S65T, A121R/W, T157E/Q/N/G, V170I, T176H/N/Q, F208W/I/L/G/S/N/A/R/T, N211Q, F208W+V170I, Y92P+F208L, Y92P+F208W, T176H+F208W, V170I+A121S, V170I+A121S+S223A, F208W+T157Q, F208W+T157N, F208W+T157S, F208W+S65T, F208W+T157E, F208W+D203C+S248C, F208I+D203C+S248C as compared to SEQ ID No 1.

According to a particular embodiment, the esterase further comprises at least one substitution, in addition to one or more of the above listed substitutions, at a position selected from G59, Y60, T61, D63, S66, F90, Y92, H129, G132, W155 and V177. Advantageously, the additional substitution is selected from Y60M/F, T61M/V, D63N/Q, S66H, F90W, and Y92G/N/P/Q/T.

In another particular embodiment, the esterase comprises at least one substitution selected from the group consisting of Y60M, T61M/V, D63N/Q, S66H, F90W, and Y92G/N/P/Q/T.

In another particular embodiment, the esterase variant comprises at least two substitutions at positions selected from G53, P58, G59, Y60, T61, A62, D63, A64, S65, S66, L67, A68, N85, T86, R89, F90, D91, Y92, P93, R96, A121, G128, H129, M131, G132, G133, G134, L152, T153, P154, W155, H156, T157, V170, T176, V177, A178, H183, S206, F208, A209, P210, S223 and N211.

It is another object of the invention to provide a nucleic acid encoding an esterase of the invention. The present invention also relates to an expression cassette or an expression vector comprising said nucleic acid, and to a host cell comprising said nucleic acid, expression cassette or vector.

It is a further object of the invention to provide a method of producing an esterase of the invention comprising:

(a) culturing the host cell according to the invention under conditions suitable to express a nucleic acid encoding an esterase; and optionally (b) recovering said esterase from the cell culture.

The present invention also relates to a method of degrading a plastic product containing at least one polyester comprising (a) contacting the plastic product with an esterase or host cell according to the invention, thereby degrading the plastic product; and optionally (b) recovering monomers and/or oligomers.

DETAILED DESCRIPTION OF THE INVENTION

Definitions

The present disclosure will be best understood by reference to the following definitions.

Herein, the terms "peptide", "polypeptide", "protein", "enzyme" refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

The term "esterase" refers to an enzyme which belongs to a class of hydrolases classified as EC 3.1.1 according to Enzyme Nomenclature that catalyzes the hydrolysis of esters into an acid and an alcohol. The term "cutinase" or "cutin hydrolase" refers to the esterases classified as EC 3.1.1.74 according to Enzyme Nomenclature that is able to catalyse the chemical reaction of production of cutin monomers from cutin and water.

The terms "wild-type protein" or "parent protein" are used interchangeably and refer to the non-mutated version of a polypeptide as it appears naturally. In the present case, the parent esterase refers to the esterase having the amino acid sequence as set forth in SEQ ID No 1.

Accordingly, the terms "mutant" and "variant" may be used interchangeably to refer to polypeptides derived from SEQ ID No 1 and comprising a modification or an alteration, i.e., a substitution, insertion, and/or deletion, at one or more (e.g., several) positions and having a polyester degrading activity. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction.

The term "modification" or "alteration" as used herein in relation to a position or amino acid means that the amino acid in the particular position has been modified compared to the amino acid of the wild-type protein.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methyllysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The sign "+" indicates a combination of substitutions. In the present document, the following terminology is used to designate a substitution: L82A denotes that amino acid residue (Leucine, L) at position 82 of the parent sequence is changed to an Alanine (A). A121V/I/M denotes that amino acid residue (Alanine, A) at position 121 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

The term "deletion", used in relation to an amino acid, means that the amino acid has been removed or is absent.

The term "insertion" means that one or more amino acids have been added.

Unless otherwise specified, the positions disclosed in the present application are numbered by reference to the amino acid sequence set forth in SEQ ID No 1.

As used herein, the term "sequence identity" or "identity" refers to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or Worldwide Web site ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

The "protein conformation" or "crystal structure" refers to the three dimensional structure of the protein.

The term "recombinant" refers to a nucleic acid construct, a vector, a polypeptide or a cell produced by genetic engineering.

The term "expression", as used herein, refers to any step involved in the production of a polypeptide including, but being not limited to, transcription, post-transcriptional modification, translation, post-translational modification, and secretion.

The term "expression cassette" denotes a nucleic acid construct comprising a coding region, i.e. a nucleic acid of the invention, and a regulatory region, i.e. comprising one or more control sequences, operably linked.

As used herein, the term "expression vector" means a DNA or RNA molecule that comprises an expression cassette of the invention. Preferably, the expression vector is a linear or circular double stranded DNA molecule.

A "polymer" refers to a chemical compound or mixture of compounds whose structure is constituted of multiple monomers (repeat units) linked by covalent chemical bonds. Within the context of the invention, the term polymer includes natural or synthetic polymers, constituted of a single type of repeat unit (i.e., homopolymers) or of a mixture of different repeat units (i.e., copolymers or heteropolymers). According to the invention, "oligomers" refer to molecules containing from 2 to about 20 monomers.

In the context of the invention, a "polyester containing material" or "polyester containing product" refers to a product, such as plastic product, comprising at least one polyester in crystalline, semi-crystalline or totally amorphous forms. In a particular embodiment, the polyester containing material refers to any item made from at least one plastic material, such as plastic sheet, tube, rod, profile, shape, film, massive block etc., which contains at least one polyester, and possibly other substances or additives, such as plasticizers, mineral or organic fillers. In another particular embodiment, the polyester containing material refers to a plastic compound, or plastic formulation, in a molten or solid state, suitable for making a plastic product.

In the present description, "polyesters" encompass but is not limited to polyethylene terephthalate (PET), polytrimethylene terephthalate (PTT), polybutylene terephthalate (PBT), polyethylene isosorbide terephthalate (PEIT), polylactic acid (PLA), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA), polyethylene naphthalate (PEN) and blends/mixtures of these polymers.

Novel Esterases with Improved Activity

The present invention provides novel esterases with improved activity. More particularly, the inventors have designed novel enzymes having superior properties for use in industrial processes. With the aim to improve the activity of esterases in conditions where industrial degradation of plastic products can be performed, the inventors have developed novel esterases derived from the esterase of SEQ ID No 1 that show higher activity compared to this parent esterase. The esterases of the invention are particularly suited to degrade plastic product containing PET. The esterases of the invention exhibit an increased specific activity and/or an increased ability to adsorb on a polymer, compared to the esterase of SEQ ID No 1. Interestingly, the inventors have identified specific amino acid residues, which are intended to be in contact with a polymer substrate in the crystal structure of the protein that may be advantageously modified to promote the contact of the substrate with the protein and thereby increasing the adsorption of the polymer and/or the activity of the protein on this polymer.

It is thus an object of the present invention to provide an esterase which (i) has at least 75%, 80%, 85%, 90%, 95% or 99% identity to the full length amino acid sequence set forth in SEQ ID No 1, (ii) contains at least one amino acid modification as compared to SEQ ID NO: 1, and (iii) exhibits increased polyester degrading activity as compared to the esterase of SEQ ID No 1.

Within the context of the invention, the term "increased activity" or "increased degrading activity" indicates an increased ability of the enzyme to degrade a plastic product or material, and more particularly a polyester containing plastic product or material, as compared to the esterase of SEQ ID No 1. Such an increase is typically of about 1-fold, 2-fold, 3-fold, 4-fold, 5-fold, or more. Particularly, the esterase variant has a polyester degrading activity at least 10% greater than the polyester degrading activity of the esterase of SEQ ID No 1, preferably at least 20%, 50%, 100%, 200%, 300%, or more greater.

The activity of a protein may be evaluated by the one skilled in the art, according to methods known per se in the art. For instance, the activity can be assessed by the measurement of the specific esterase activity rate, the measurement of the specific polyester's depolymerization activity rate, the measurement of the rate to degrade a solid polyester compound dispersed in an agar plate, or the measurement of the specific polyester's depolymerization activity rate in reactor.

Within the context of the invention, the terms "specific activity" or "specific degrading activity" designate the initial rate of oligomers and/or monomers released under suitable conditions of temperature, pH and buffer, when contacting the polyester containing plastic product with a degrading enzyme, such as an esterase according to the invention. As an example, the specific activity of PET hydrolysis corresponds to µmol of PET hydrolysed/min or mg of equivalent TA produced/hour and per mg of enzyme as determined in the linear part of the hydrolysis curve.

The ability of a protein to adsorb on a substrate may be evaluated by the one skilled in the art, according to methods known per se in the art. For instance, the proteic content or the residual esterase activity, residual polyester's depolymerization activity, residual degradation of a solid polyester compound dispersed in an agar plate, or residual polyester's depolymerization activity in reactor can be measured from a solution containing the esterase of the invention and wherein the esterase has been previously incubated with a substrate under suitable conditions where no enzymatic reaction can occur.

In a particular embodiment, the variants of the invention have both an improved thermostability and an increased polyester degrading activity as compared to the esterase of SEQ ID No 1.

Within the context of the invention, the term "increased thermostability" indicates an increased ability of the enzyme to resist to changes in its chemical and/or physical structure at high temperatures, and more particularly at temperature between 50° C. and 90° C., as compared to the esterase of SEQ ID No 1. Such an increase is typically of about 1-fold, 2-fold, 3-fold, 4-fold, 5-fold, or more. Particularly, the esterases of the present invention may exhibit an increased melting temperature (Tm) as compared to the esterase of SEQ ID No 1. In the context of the present invention, the melting temperature refers to the temperature at which half of the protein/enzyme population considered is unfolded or misfolded. Typically, the esterase of the invention shows an increased Tm of about 1° C., 2° C., 3° C., 4° C., 5° C., 10° C. or more, as compared to the Tm of the esterase of SEQ ID No 1.

In particular, the esterases of the present invention can have an increased half-life at a temperature between 50° C. and 90° C., as compared to the esterase of SEQ ID No 1.

Furthermore, at such temperature, the esterases of the invention may exhibit greater degrading activity as compared to the esterase of SEQ ID No 1.

The thermostability of a protein may be evaluated by the one skilled in the art, according to methods known per se in the art. For instance, thermostability can be assessed by analysis of the protein folding using circular dichroism. Alternatively or in addition, thermostability can be assessed by measuring the residual esterase activity and/or the residual polyester depolymerization activity of the enzyme after incubation at different temperatures. The ability to perform multiple rounds of polyester's depolymerization assays at different temperatures can also be evaluated. A rapid and valuable test may consist on the evaluation, by halo diameter measurement, of the enzyme ability to degrade a solid polyester compound dispersed in an agar plate after incubation at different temperatures. Preferably, a Differential Scanning Fluorimetry (DSF) is performed to assess the thermostability of a protein/enzyme. More particularly, the DSF may be used to quantify the change in thermal denaturation temperature of a protein and thereby to determine its melting temperature (Tm). In the context of the invention, and unless specific indications, the Tm is measured using DSF as exposed in the experimental part. In the context of the invention, comparisons of Tm are performed with Tm that are measured under same conditions (e.g. pH, nature and amount of polyesters, etc.).

The esterases of the invention may comprise one or several modifications as disclosed below.

According to the invention, the esterase is a variant of the esterase of SEQ ID No 1, which has at least 75%, 80%, 85%, 90%, 95% or 99% identity to the full length amino acid sequence set forth in SEQ ID No 1, and which has at least one substitution at a position selected from G53, P58, A62, A64, S65, L67, A68, N85, T86, R89, D91, P93, R96, A121, G128, M131, G133, G134, L152, T153, P154, H156, T157, V170, T176, A178, P179, H183, S206, F208, A209, P210, N211, or S223 wherein the positions are numbered by reference to the amino acid sequence set forth in SEQ ID No 1.

According to the invention, the targeted amino acid(s) may be replaced by any one of the 19 other amino acids.

Preferably, the esterase variant comprises a least one substitution at a position selected from G53, A62, A64, S65, A68, N85, T86, R89, A121, T157, V170, T176, S206, F208, N211, S223.

More preferably, the esterase variant comprises at least one substitution at a position selected from G53, S65, A121, T157, V170, T176, F208 or N211.

In a particular embodiment, the esterase variant comprises a least one substitution selected from G53L, S65T, A121R/W, T157E/Q/N/G, V170I, T176H/N/Q, F208W/I/L/G/S/N/A/R/T and N211Q. Preferably, the esterase variant comprises at least one substitution selected from F208W/I/L. In a preferred embodiment, the esterase variant comprises a least the substitution F208W. In another preferred embodiment, the esterase variant comprises at least the substitution F208I.

In a particular embodiment, the esterase variant further comprises, in addition to at least one substitution described above, at least one additional substitution at a position selected from G59, Y60, T61, D63, S66, F90, Y92, H129, G132, W155 and V177. Preferably, the one or more additional substitutions are selected from Y60M/F, T61M/V, D63N/Q, S66H, F90W, and Y92G/N/P/Q/T.

Alternatively or in addition, at least one of the additional substitution is selected from A121S, T157S or S223A.

In another particular embodiment, the esterase variant comprises at least one substitution, and in particular a single substitution, as compared to SEQ ID No 1 at positions selected from Y60, G53, T61, A62, D63, S65, S66, F90, Y92, A121, H129, T157, T176, V170, V177, F208, N211, and wherein the substitutions are different from Y60A/F, T61A/G, A62G/S, D63T/R, S66A, F90A/R/Y, Y92A, H129W and V177A. Preferably, the esterase comprises one or more substitutions selected from the group consisting of Y60M, T61M/V, D63N/Q, S66H, F90W, and Y92G/N/P/Q/T. In another particular embodiment, the esterase comprises a single substitution selected from the group consisting of Y60M, T61M/V, D63N/Q, S66H, F90W, and Y92G/N/P/Q/T.

According to a particular embodiment, the variant comprises at least one substitution selected from D63N/Q.

According to a particular embodiment, the variant comprises at least one substitution selected from Y92G/N/P/Q/T, preferably Y92P.

In another particular embodiment, the esterase variant comprises at least one substitution at a position selected from D63, A64, A68, N85, R89, W155, T176, S206, F208 or N211.

In another particular embodiment, the esterase variant comprises at least two substitutions at positions selected from G53, P58, G59, Y60, T61, A62, D63, A64, S65, S66, L67, A68, N85, T86, R89, F90, D91, Y92, P93, R96, A121, G128, H129, M131, G132, G133, G134, L152, T153, P154, W155, H156, T157, V170, T176, V177, A178, H183, S206, F208, A209, P210, S223 and N211.

In another particular embodiment, the esterase variant comprises at least two substitutions at positions selected from G53, Y60, T61, D63, S65, S66, F90, Y92, A121, T157, V170, T176, V177, F208, S223 and N211.

Particularly, the esterase variant comprises at least two substitutions at positions selected from S65, Y92, A121, T157, V170, T176, F208 and S223.

According to a particular embodiment, the variant comprises at least the combination of substitutions consisting of F208W+V170I.

According to a particular embodiment, the variant comprises at least the combination of substitutions consisting of Y92P+F208L.

According to a particular embodiment, the variant comprises at least the combination of substitutions consisting of Y92P+F208W.

According to a particular embodiment, the variant comprises at least the combination of substitutions consisting of T176H+F208W.

According to a particular embodiment, the variant comprises at least the combination of substitutions consisting of V170I+A121S.

According to a particular embodiment, the variant comprises at least the combination of substitutions consisting of V170I+A121S+S223A.

According to a particular embodiment, the variant comprises at least the combination of substitutions consisting of F208W+T157Q.

According to a particular embodiment, the variant comprises at least the combination of substitutions consisting of F208W+T157N.

According to a particular embodiment, the variant comprises at least the combination of substitutions consisting of F208W+T157S.

According to a particular embodiment, the variant comprises at least the combination of substitutions consisting of F208W+S65T.

According to a particular embodiment, the variant comprises at least the combination of substitutions consisting of F208W+T157E.

In a particular embodiment, the esterase variant of the invention comprises one or several modifications and/or mutations as listed above.

Novel Esterases with Improved Activity and Thermostability. It is a further object of the invention to provide novel esterases that exhibit both increased polyester degrading activity and increased thermostability as compared to the esterase of SEQ ID No 1.

It is another object of the invention to provide an esterase which (i) has at least 75%, 80%, 85%, 90%, 95% or 99% identity to the full length amino acid sequence set forth in SEQ ID No 1, (ii) contains at least one amino acid modification as compared to SEQ ID NO: 1, and (iii) exhibits both an increased thermostability and an increased activity as compared to the esterase of SEQ ID No 1.

Advantageously, the variant comprises at least one substitution selected from T61M, Y92G/P, F208W, Y92P+F208W, and F208W+V170I and exhibits both an increased thermostability and an increased activity as compared to the esterase of SEQ ID No 1.

Advantageously, the esterase variant comprises at least one mutation as disclosed above and at least one additional substitution at a position selected from D203C+S248C by reference to SEQ ID No 1. Advantageously, the variant comprises at least the substitution(s) selected from F208W+D203C+S248C or F208I+D203C+S248C and exhibits both an increased thermostability and an increased activity as compared to the esterase of SEQ ID No 1.

Polyester Degrading Activity of the Variant

It is an object of the invention to provide new enzymes having an esterase activity. In a particular embodiment, the enzyme of the invention further exhibits a cutinase activity.

In a particular embodiment, the esterase of the invention has a polyester degrading activity, preferably a polyethylene terephthalate degrading activity.

In another particular embodiment, the esterase of the invention also has a PBAT degrading activity.

Advantageously, the esterase variant of the invention exhibits a polyester degrading activity at least in a range of temperatures from 20° C. to 90° C., preferably from 40° C. to 80° C., more preferably from 50° C. to 70° C., even more preferably from 60° C. to 70° C., even more preferably at 65° C. In a particular embodiment, the esterase variant of the invention exhibits a polyester degrading activity at 70° C. In a particular embodiment, the polyester degrading activity is still measurable at a temperature between 60° C. and 90° C.

In a particular embodiment, the esterase variant of the invention has an increased polyester degrading activity at a given temperature, compared to the esterase of SEQ ID No 1, and more particularly at a temperature between 40° C. and 80° C., more preferably between 50° C. and 70° C., even more preferably between 60° C. and 70° C., even more preferably at 65° C. In a particular embodiment, the esterase variant has a polyester degrading activity at 65° C. at least 5% higher than the polyester degrading activity of the esterase of SEQ ID No 1, preferably at least 10%, 20%, 50%, 100%, 200%, 300%, or more higher. In a particular embodiment, the esterase variant has a polyester degrading activity at 65° C. at least 10% greater than the polyester degrading activity of the esterase of SEQ ID No 1, preferably at least 20%, 50%, 100%, 200%, 300%, or more greater.

In a particular embodiment, the esterase variant of the invention exhibits a measurable esterase activity at least in a range of pH from 5 to 11, preferably in a range of pH from 6 to 9, more preferably in a range of pH from 6.5 to 9, even more preferably in a range of pH from 6.5 to 8.

Nucleic Acids, Expression Cassette, Vector, Host Cell

It is a further object of the invention to provide a nucleic acid encoding an esterase as defined above.

As used herein, the term "nucleic acid", "nucleic sequence," "polynucleotide", "oligonucleotide" and "nucleotide sequence" are used interchangeably and refer to a sequence of deoxyribonucleotides and/or ribonucleotides. The nucleic acids can be DNA (cDNA or gDNA), RNA, or a mixture of the two. It can be in single stranded form or in duplex form or a mixture of the two. It can be of recombinant, artificial and/or synthetic origin and it can comprise modified nucleotides, comprising for example a modified bond, a modified purine or pyrimidine base, or a modified sugar. The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding an esterase as defined above. Preferably, such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding an esterase of the invention, wherein the sequence of said nucleic acids, or a portion of said sequence at least, has been engineered using optimized codon usage.

Alternatively, the nucleic acids according to the invention may be deduced from the sequence of the esterase according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

Nucleic acids of the invention may further comprise additional nucleotide sequences, such as regulatory regions, i.e., promoters, enhancers, silencers, terminators, signal peptides and the like that can be used to cause or regulate expression of the polypeptide in a selected host cell or system.

The present invention further relates to an expression cassette comprising a nucleic acid according to the invention operably linked to one or more control sequences that direct the expression of said nucleic acid in a suitable host cell. Typically, the expression cassette comprises, or consists of, a nucleic acid according to the invention operably linked to a control sequence such as transcriptional promoter and/or transcription terminator. The control sequence may include a promoter that is recognized by a host cell or an in vitro expression system for expression of a nucleic acid encoding an esterase of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. The control sequence may also be a transcription terminator, which is recognized by a host cell to terminate transcription. The terminator is operably linked to the 3'-terminus of the nucleic acid encoding the esterase. Any terminator that is functional in the host cell may be used in the present invention. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA molecule used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally present operator. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. The choice of the vector will typically depend on the compatibility of the vector with the host cell into which the vector is to be introduced.

It is another object of the invention to provide a host cell comprising a nucleic acid, an expression cassette or a vector as described above. The present invention thus relates to the use of a nucleic acid, expression cassette or vector according to the invention to transform, transfect or transduce a host cell. The choice of the vector will typically depend on the compatibility of the vector with the host cell into which it must be introduced.

According to the invention, the host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The term "host cell" also encompasses any progeny of a parent host cell that is not identical to the parent host cell due to mutations that occur during replication. The host cell may be any cell useful in the production of a variant of the present invention, e.g., a prokaryote or a eukaryote. The prokaryotic host cell may be any Gram-positive or Gram-negative bacterium. The host cell may also be an eukaryotic cell, such as a yeast, fungal, mammalian, insect or plant cell. In a particular embodiment, the host cell is selected from the group of *Escherichia coli*, *Bacillus*, *Streptomyces*, *Trichoderma*, *Aspergillus*, *Saccharomyces*, *Pichia* or *Yarrowia*.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation.

Optionally, more than one copy of a nucleic acid, cassette or vector of the present invention may be inserted into a host cell to increase production of the variant.

In a particular embodiment, the host cell is a recombinant microorganism. The invention indeed allows the engineering of microorganisms with improved capacity to degrade polyester containing material. For instance, the sequence of the invention may be used to complement a wild type strain of a fungus or bacterium already known as able to degrade polyester, in order to improve and/or increase the strain capacity.

Production of Esterase Variant

It is another object of the invention to provide a method of producing the esterase variant of the invention, comprising expressing a nucleic acid encoding the esterase and optionally recovering the esterase.

In particular, the present invention relates to in vitro methods of producing an esterase of the present invention comprising (a) contacting a nucleic acid, cassette or vector of the invention with an in vitro expression system; and (b) recovering the esterase produced. In vitro expression systems are well-known by the person skilled in the art and are commercially available.

Preferably, the method of production comprises:

(a) culturing a host cell that comprises a nucleic acid encoding an esterase of the invention under conditions suitable to express the nucleic acid; and optionally (b) recovering said esterase from the cell culture.

Advantageously, the host cell is a recombinant *Bacillus*, recombinant *E. coli*, recombinant *Aspergillus*, recombinant *Trichoderma*, recombinant *Streptomyces*, recombinant *Saccharomyces*, recombinant *Pichia* or recombinant *Yarrowia lipolytica*.

The host cells are cultivated in a nutrient medium suitable for production of polypeptides, using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the enzyme to be expressed and/or isolated. The cultivation takes place in a suitable nutrient medium, from commercial suppliers or prepared according to published compositions (e.g., in catalogues of the American Type Culture Collection).

If the esterase is excreted into the nutrient medium, the esterase can be recovered directly from the culture supernatant. Conversely, the esterase can be recovered from cell lysates or after permeabilisation. The esterase may be recovered using any method known in the art. For example, the esterase may be recovered from the nutrient medium by conventional procedures including, but not limited to, collection, centrifugation, filtration, extraction, spray-drying, evaporation, or precipitation. Optionally, the esterase may be partially or totally purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction to obtain substantially pure polypeptides.

The esterase may be used as such, in purified form, either alone or in combinations with additional enzymes, to catalyze enzymatic reactions involved in the degradation and/or recycling of a polyester containing material, such as plastic products containing polyester. The esterase may be in soluble form, or on solid phase. In particular, it may be bound to cell membranes or lipid vesicles, or to synthetic supports such as glass, plastic, polymers, filter, membranes, e.g., in the form of beads, columns, plates and the like.

Composition

It is a further object of the invention to provide a composition comprising an esterase or a host cell of the invention. In the context of the invention, the term "composition" encompasses any kind of compositions comprising an esterase of the invention. In a particular embodiment, the esterase is in isolated or at least partially purified form.

The composition may be liquid or dry, for instance in the form of a powder. In some embodiments, the composition is a lyophilisate. For instance, the composition may comprise the esterase and/or recombinant cells encoding the esterase of the invention or extract thereof, and optionally excipients and/or reagents etc. Appropriate excipients encompass buffers commonly used in biochemistry, agents for adjusting pH, preservatives such as sodium benzoate, sodium sorbate or sodium ascorbate, conservatives, protective or stabilizing agents such as starch, dextrin, arabic gum, salts, sugars e.g. sorbitol, trehalose or lactose, glycerol, polyethyleneglycol, polyethene glycol, polypropylene glycol, propylene glycol, sequestering agent such as EDTA, reducing agents, amino acids, a carrier such as a solvent or an aqueous solution, and the like. The composition of the invention may be obtained by mixing the esterase with one or several excipients.

The composition of the invention may comprise from 0.1% to 99.9%, preferably from 0.1% to 50%, more preferably from 0.1% to 30%, even more preferably from 0.1% to 5% by weight of the esterase of the invention and from 0.1% to 99.9%, preferably from 50% to 99.9%, more preferably from 70% to 99.9%, even more preferably from 95% to 99.9% by weight of excipient(s). A preferred composition comprises between 0.1 and 5% by weight of the esterase of the invention.

In a particular embodiment, the composition may further comprise additional polypeptide(s) exhibiting an enzymatic activity. The amounts of esterase of the invention will be easily adapted by those skilled in the art depending e.g., on the nature of the polyester containing material to degrade and/or the additional enzymes/polypeptides contained in the composition.

In a particular embodiment, the esterase of the invention is solubilized in an aqueous medium together with one or several excipients, especially excipients which are able to stabilize or protect the polypeptide from degradation. For instance, the esterase of the invention may be solubilized in water, eventually with additional components, such as glycerol, sorbitol, dextrin, starch, glycol such as propanediol, salt, etc. The resulting mixture may then be dried so as to obtain a powder. Methods for drying such mixture are well known to the one skilled in the art and include, without limitation, lyophilisation, freeze-drying, spray-drying, supercritical drying, down-draught evaporation, thin-layer evaporation, centrifugal evaporation, conveyer drying, fluidized bed drying, drum drying or any combination thereof.

In a further particular embodiment, the composition of the invention comprises at least one recombinant cell expressing an esterase of the invention, or an extract thereof. An "extract of a cell" designates any fraction obtained from a cell, such as cell supernatant, cell debris, cell walls, DNA extract, enzymes or enzyme preparation or any preparation derived from cells by chemical, physical and/or enzymatic treatment, which is essentially free of living cells. Preferred extracts are enzymatically-active extracts. The composition of the invention may comprise one or several recombinant cells of the invention or extract thereof, and optionally one or several additional cells.

In a particular embodiment, the composition consists or comprises a lyophilized culture medium of a recombinant microorganism expressing and excreting an esterase of the invention. In a particular embodiment, the powder comprises the esterase of the invention and a stabilizing/solubilizing amount of glycerol, sorbitol or dextrin, such as maltodextrine and/or cyclodextrine, starch, glycol such as propanediol, and/or salt.

Use of the Esterase of the Invention

It is a further object of the invention to provide methods using an esterase of the invention for degrading in aerobic or anaerobic conditions and/or recycling polyester containing material, as plastic products made of or containing polyesters. The variant esterases of the invention are particularly useful for degrading a plastic product comprising PET.

It is therefore an object of the invention to use an esterase of the invention, or corresponding recombinant cell or extract thereof, or composition for the enzymatic degradation of a polyester containing material, such as a PET containing material.

It is another object of the invention to provide a method for degrading a plastic product containing at least one polyester, wherein the plastic product is contacted with an esterase or host cell or composition of the invention, thereby degrading the plastic product. Advantageously, polyester(s) of the polyester containing material is (are) depolymerized up to monomers and/or oligomers.

In an embodiment of the method of degradation, at least one polyester is degraded to yield repolymerizable monomers and/or oligomers, which are advantageously retrieved in order to be reused.

In an embodiment, polyester(s) of the polyester containing material is (are) fully degraded.

In a particular embodiment, the plastic product comprises at least one polyester selected from polyethylene terephthalate (PET), polytrimethylene terephthalate (PTT), polybutylen terephthalate (PBT), polyethylene isosorbide terephthalate (PEIT), polylactic acid (PLA), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA), polyethylene naphthalate (PEN) and blends/mixtures of these materials, preferably polyethylene terephthalate. In a preferred embodiment, the polyester containing material comprises PET, and at least monomers such as monoethylene glycol or terephthalic acid, and/or oligomers such as methyl-2-hydroxyethyl terephthalate (MHET), bis(2-hydroxyethyl) terephthalate (BHET), 2-hydroxyethyl benzoate (HEB) and dimethyl terephthalate (DMT) are recovered for recycling or methanisation for instance.

The invention also relates to a method of producing monomers and/or oligomers from a polyester containing material, comprising exposing a polyester containing material to an esterase of the invention, or corresponding recombinant cell or extract thereof, or composition, and optionally recovering monomers and/or oligomers. The method of the invention is particularly useful for producing monomers selected from monoethylene glycol and terephthalic acid, and/or oligomers selected from methyl-2-hydroxyethyl terephthalate (MHET), bis(2-hydroxyethyl) terephthalate (BHET), 2-hydroxyethyl benzoate (HEB) and dimethyl terephthalate (DMT).

The time required for degrading a polyester containing material may vary depending on the polyester containing material itself (i.e., nature and origin of the plastic product, its composition, shape etc.), the type and amount of esterase used, as well as various process parameters (i.e., temperature, pH, additional agents, etc.). One skilled in the art may easily adapt the process parameters to the polyester containing material.

Advantageously, the degrading process is implemented at a temperature comprised between 20° C. and 90° C., preferably between 40° C. and 80° C., more preferably between 50° C. and 70° C., more preferably between 60° C. and 70° C., even more preferably at 65° C. In another particular embodiment, the degrading process is implemented at 70° C. More generally, the temperature is maintained below an inactivating temperature, which corresponds to the temperature at which the esterase is inactivated and/or the recombinant microorganism does no more synthesize the esterase. Particularly, the temperature is maintained below the glass transition temperature (Tg) of the polyester in the polyester containing material. More particularly, the process is implemented in a continuous way, at a temperature at which the esterase can be used several times and/or recycled.

Advantageously, the degrading process is implemented at a pH comprised between 5 and 11, preferably at a pH between 6 and 9, more preferably at a pH between 6.5 and 9, even more preferably at a pH between 6.5 and 8.

In a particular embodiment, the polyester containing material may be pretreated prior to be contacted with the esterase, in order to physically change its structure, so as to increase the surface of contact between the polyester and the variant of the invention.

Optionally, monomers and/or oligomers resulting from the depolymerization may be recovered, sequentially or continuously. A single type of monomers and/or oligomers or several different types of monomers and/or oligomers may be recovered, depending on the starting polyester containing material.

The recovered monomers and/or oligomers may be further purified, using all suitable purifying methods and conditioned in a re-polymerizable form. Examples of purifying methods include stripping process, separation by aqueous solution, steam selective condensation, filtration and concentration of the medium after the bioprocess, separation, distillation, vacuum evaporation, extraction, electrodialysis, adsorption, ion exchange, precipitation, crystallization, concentration and acid addition dehydration and precipitation, nanofiltration, acid catalyst treatment, semi continuous mode distillation or continuous mode distillation, solvent extraction, evaporative concentration, evaporative crystallization, liquid/liquid extraction, hydrogenation, azeotropic distillation process, adsorption, column chromatography, simple vacuum distillation and microfiltration, combined or not.

The repolymerizable monomers and/or oligomers may then be reused for instance to synthesize polyesters. Advantageously, polyesters of same nature are repolymerized. However, it is possible to mix the recovered monomers and/or oligomers with other monomers and/or oligomers, in order for instance to synthesize new copolymers. Alternatively, the recovered monomers may be used as chemical intermediates in order to produce new chemical compounds of interest.

The invention also relates to a method of surface hydrolysis or surface functionalization of a polyester containing material, comprising exposing a polyester containing material to an esterase of the invention, or corresponding recombinant cell or extract thereof, or composition. The method of the invention is particularly useful for increasing hydrophilicity, or water absorbency, of a polyester material. Such increased hydrophilicity may have particular interest in textiles production, electronics and biomedical applications.

It is a further object of the invention to provide a polyester containing material in which an esterase of the invention and/or a recombinant microorganism expressing and excreting said esterase is/are included. In a particular embodiment, such polyester containing material may be a plastic compound. It is thus an object of the invention to provide a plastic compound containing an esterase of the invention and/or a recombinant cell and/or a composition or extract thereof and at least one polyester. In a preferred embodiment, the polyester is PET.

EXAMPLES

Example 1—Construction, Expression and Purification of Esterases

Construction

The esterase variants have been generated using the plasmidic construction pET26b-LCC-His. This plasmid consists in cloning a gene encoding the esterase of SEQ ID No 1, optimized for *Escherichia coli* expression between NdeI and XhoI restriction sites. Two site directed mutagenesis kits have been used according to the recommendations of the supplier, in order to generate the esterase variants: QuikChange II Site-Directed Mutagenesis kit and QuikChange Lightning Multi Site-Directed from Agilent (Santa Clara, Calif., USA).

Expression and Purification of the Esterases

The strains Stellar™ (Clontech, Calif., USA) and *E. coli* One Shot® BL21 DE3 (Life technologies, Carlsbad, Calif., USA) have been successively employed to perform the cloning and recombinant expression in 50 mL LB-Miller medium or ZYM auto inducible medium (Studier et al., 2005—Prot. Exp. Pur. 41, 207-234). The induction in LB-Miller medium has been performed at 16° C., with 0.5 mM of isopropyl 3-D-1-thiogalactopyranoside (IPTG, Euromedex, Souffelweyersheim, France). The cultures have been stopped by centrifugation (8000 rpm, 20 minutes at 10° C.) in an Avanti J-26 XP centrifuge (Beckman Coulter, Brea, USA). The cells have been suspended in 20 mL of Talon buffer (Tris-HCl 20 mM, NaCl 300 mM, pH 8). Cell suspension was then sonicated during 2 minutes with 30% of amplitude (2 sec ON and 1 sec OFF cycles) by FB 705 sonicator (Fisherbrand, Illkirch, France). Then, a step of centrifugation has been realized: 30 minutes at 11000 rpm, 10° C. in an Eppendorf centrifuge. The soluble fraction has been collected and submitted to affinity chromatography. This purification step has been completed with Talon® Metal Affinity Resin (Clontech, Calif., USA). Protein elution has been carried out with gradient of Talon buffer supplemented with imidazole. Purified protein has been dialyzed against Talon buffer then quantified using Bio-Rad protein assay according to manufacturer instructions (Lifescience Bio-Rad, France) and stored at +4° C.

Example 2—Evaluation of the Activity of the Esterases

The specific activity of the esterase has been determined and compared to the specific activity of the esterase of SEQ ID No 1.

Multiple methodologies to assess the specific activity have been used:

(1) Specific activity based upon the pNP-Butyrate hydrolysis;
(2) Specific activity based upon PET hydrolysis;
(3) Specific activity based upon the degradation of a polyester under solid form;
(4) Specific activity based upon PET hydrolysis in reactors.

2.1 pNP-Butyrate Hydrolysis

20 µL of protein in solution has been combined to 175 µL of 0.1M potassium phosphate buffer pH 8.0 and 5 µL of pNP-Butyrate (40 mM in 2-methyl-2-butanol). Enzymatic reaction has been performed at 30° C. under agitation, during 15 minutes and absorbance at 405 nm acquired by microplate spectrophotometer (Versamax, Molecular Devices, Sunnyvale, Calif., USA). Specific activity (initial velocity expressed in mol of released pNP/min/mg enzyme) has been determined in the linear part of the hydrolysis curve and used to compare activity of the wild type esterase with the activity of the variants.

2.2 PET Hydrolysis 100 mg of amorphous PET were weighted and introduced in a 100 mL glass bottle. 1 mL of esterase preparation (as reference control) or variant preparation respectively, prepared at 0.02 or 0.03 mg/mL in Talon buffer (Tris-HCl 20 mM, NaCl 0.3M, pH 8) and introduced in the glass bottle. Finally, 49 mL of 0.1 M potassium phosphate buffer pH 8 was added.

The depolymerization started by incubating each glass bottle at 65° C. and 150 rpm in a Max Q 4450 incubator (Thermo Fisher Scientific, Inc. Waltham, Mass., USA).

The initial rate of depolymerization reaction, in mg of equivalent TA generated/hour, was determined by samplings performed at different time during the first 24 hours and analyzed by Ultra High Performance Liquid Chromatography (UHPLC). If necessary, samples were diluted in 0.1 M potassium phosphate buffer pH 8. Then, 150 µL of methanol and 6.5 µL of HCl 6 N were added to 150 µL of sample or dilution. After mixing and filtering on 0.45 m syringe filter, samples were loaded on UHPLC to monitor the liberation of terephthalic acid (TA), MHET and BHET. Chromatography system used was an Ultimate 3000 UHPLC system (Thermo Fisher Scientific, Inc. Waltham, Mass., USA) including a pump module, an autosampler, a column oven thermostated at 25° C., and an UV detector at 240 nm. The column used was a Discovery® HS C18 HPLC Column (150×4.6 mm, 5 m, equipped with precolumn, Supelco, Bellefonte, USA). TA, MHET and BHET were separated using a gradient of MeOH (30% to 90%) in 1 mM of $H_2SO_4$ at 1 mL/min. Injection was 20 µL of sample. TA, MHET and BHET were measured according to standard curves prepared from commercial TA and BHET and in house synthetized MHET in the same conditions than samples. The specific activity of PET hydrolysis (mg of equivalent TA/hour/mg of enzyme) was determined in the linear part of the hydrolysis curve. Equivalent TA corresponds to the sum of TA measured and of TA contained in measured MHET and BHET.

2.3 Degradation of a Polyester Under Solid Form

20 µL of enzyme preparation was deposited in a well created in an agar plate containing PET. Preparation of agar plates was realized by solubilizing 500 mg of PET is solubilized in HFIP, and this medium is poured in a 250 mL aqueous solution. After HFIP evaporation at 52° C., the solution was mixed v/v with 0.2 M potassium phosphate buffer pH 8 containing 3% agar. Around 30 mL of the mixture is used to prepare each omnitray and stored at 4° C.

The diameters of the halos formed due to the polyester degradation by wild-type esterase and variants were measured and compared after 2 to 4 hours at 60° C. or 65° C.

2.4 PET Hydrolysis in Reactor

A Minibio 500 bioreactors (Applikon Biotechnology B. V., Delft, The Netherlands) was started with 5 g of amorphous PET and 100 mL of 10 mM potassium phosphate buffer pH 8 containing 2.5 to 5 mg of esterase. Agitation was set at 250 rpm using a marine impeller. Bioreactor was thermostated at 65° C. by immersion in an external water bath. pH was regulated at 8 by addition of KOH at 3 M. The different parameters (pH, temperature, agitation, addition of base) were monitored thanks to BioXpert software V2.95. 500 µL of reaction medium was sampled regularly.

Amount of TA, MHET and BHET was determined by HPLC, as described in example 2.2. Amount of EG was determined using an Aminex HPX-87K column (Bio-Rad Laboratories, Inc, Hercules, Calif., United States) thermostated at 65° C. Eluent was $K_2HPO_4$ 5 mM at 0.6 mL·min$^{-1}$. Injection was 20 µL. Ethylene glycol was monitored using refractometer.

The percentage of hydrolysis was calculated based on the ratio of molar concentration at a given time (TA+MHET+BHET) versus the total amount of TA contained in the initial sample, or based on the ratio of molar concentration at a given time (EG+MHET+2×BHET) versus the total amount of EG contained in the initial sample. Specific activity corresponds to specific rate of degradation, and is calculated in mg of total liberated equivalent TA per hour and per mg of enzyme or in mg of total equivalent EG per hour and per mg of enzyme.

Compared specific degrading activities of esterase variants of the invention are shown in Table 1. The specific degrading activity of the esterase of SEQ ID No 1 is used as a reference and considered as 100% degrading activity. The degrading activity is measured as exposed in example 2.2 (mg of equivalent TA/hour/mg of enzyme).

TABLE 1

Specific activity of esterase variants of the invention

| Variant of the invention | Specific activity |
| --- | --- |
| D63N | 147% |
| D63Q | 139% |
| F90W | 112% |
| F208I | 156% |
| F208L | 133% |
| F208W | 143% |
| N211Q | 112% |
| S65T | 118% |
| S66H | 113% |
| T157E | 114% |
| T157G | 116% |
| T157N | 132% |
| T157Q | 124% |
| T176H | 128% |
| T176N | 110% |
| T176Q | 144% |
| T61M | 121% |

TABLE 1-continued

Specific activity of esterase variants of the invention

| Variant of the invention | Specific activity |
|---|---|
| T61V | 130% |
| Y92G | 120% |
| Y92N | 112% |
| Y92P | 177% |
| Y92Q | 155% |
| Y92T | 126% |
| Y60M | 128% |
| G53L | 153% |
| A121R | 132% |
| A121W | 147% |
| V170I | 141% |
| F208G | 111% |
| F208S | 112% |
| F208N | 114% |
| F208A | 143% |
| F208R | 121% |
| F208T | 130% |
| F208W + V170I | 128% |
| Y92P + F208L | 118% |
| Y92P + F208W | 116% |
| T176H + F208W | 111% |
| V170I + A121S | 111% |
| V170I + A121S + S223A | 114% |
| F208W + T157Q | 134% |
| F208W + T157N | 137% |
| F208W + T157S | 129% |
| F208W + S65T | 189% |
| F208W + T157E | 145% |
| F208W + D203C + S248C | 123% |
| F208I + D203C + S248C | 133% |

Example 3—Evaluation of the Activity and Thermostability of the Esterase Variants of the Invention The thermostability of esterase variants of the invention has been evaluated and compared with the thermostability of the esterase of SEQ ID No 1.

Differential Scanning Fluorimetry (DSF) has been Used to Estimate Thermostability DSF was used to evaluate the thermostability of the wild-type protein and variants by determining their melting temperature (Tm), temperature at which half of the protein population is unfolded. Protein samples were prepared at a concentration of 14 µM (0.4 mg/mL) and stored in buffer A consisting of 20 mM Tris HCl pH 8.0, 300 mM NaCl. The SYPRO orange dye 5000× stock solution in DMSO was first diluted to 250× in water. Protein samples were loaded onto a white clear 96-well PCR plate (Bio-Rad cat #HSP9601) with each well containing a final volume of 25 µl. The final concentration of protein and SYPRO Orange dye in each well were 5 µM (0.14 mg/ml) and 10× respectively. Loaded volumes per well were as follow: 15 µL of buffer A, 9 µL of the 0.4 mg/mL protein solution and 1 µL of the 250× Sypro Orange diluted solution. The PCR plates were then sealed with optical quality sealing tape and spun at 2000 rpm for 1 min at room temperature. DSF experiments were then carried out using a CFX96 real-time PCR system set to use the 450/490 excitation and 560/580 emission filters. The samples were heated from 25 to 100° C. at the rate of 1.1° C./min. A single fluorescence measurement was taken every 0.3° C. Melting temperatures were determined by performing a curve fit to the Boltzmann equation.

Wild-type protein and variants were then compared based on their Tm values. Due to high reproducibility between experiments on the same protein from different productions, a ΔTm of 0.8° C. was considered as significant to compare variants. Tm values correspond to the average of at least 2 measurements.

Compared specific degrading activities and thermostabilities of esterase variants of the invention are shown in Table 2. The specific degrading activity of the esterase of SEQ ID No 1 is used as a reference and considered as 100% degrading activity. The specific degrading activity is measured according to example 2.2 (mg of equivalent TA/hour/mg of enzyme). The thermostability is expressed in Tm values (measured according to example 3) and the gain of Tm as compared to the Tm of the esterase of SEQ ID No 1 is noted in brackets.

TABLE 2

Specific activity and Tm of the esterases of the invention

| Variants of the invention | Specific degrading activity | Tm of the variant of the invention |
|---|---|---|
| F208W | 143% | 85.90° C. +/− 0.17° C. (+1.20° C.) |
| Y92P | 177% | 85.80° C. +/− 0.00° C. (+1.10° C.) |
| T61M | 121% | 87.40° C. +/− 0.17° C. (+2.70° C.) |
| Y92G | 120% | 87.00° C. +/− 0.00° C. (+2.30° C.) |
| Y92P + F208W | 116% | 86.60° C. +/− 0.17° C. (+1.90° C.) |
| F208W + V170I | 128% | 85.80° C. +/− 0.00° C. (+1.10° C.) |
| F208W + D203C + S248C | 123% | 94.80° C. +/− 0.00° C. (+10.10° C.) |
| F208I + D203C + S248C | 133% | 90.90° C. +/− 0.00° C. (+6.20° C.) |

We claim:

1. An esterase variant which (i) has at least 75% identity to the full length amino acid sequence set forth in SEQ ID NO: 1, (ii) has at least one amino acid substitution at a position selected from F208, T157, T176, S65, P58, A62, A64, L67, A68, N85, T86, R89, D91, P93, R96, G128, M131, G133, G134, L152, T153, P154, H156, A178, P179, H183, S206, A209, P210, N211, W155, Y60, T61, D63, S66, F90, Y92, H129, V177 wherein the substitutions are different from Y60A/F, T61A/G, A62G/S, D63T/R, S66A, F90A/R/Y, Y92A, H129W and V177A or at least one amino acid substitution selected from G53L, A121R/W and V170I, wherein the positions are numbered by reference to the amino acid sequence set forth in SEQ ID NO: 1 and (iii) exhibits a polyester degrading activity.

2. The esterase variant according to claim 1, wherein said esterase comprises at least one amino acid substitution at a position selected from the group consisting of Y60, T61, A62, D63, S66, F90, Y92, F208, T157, T176, S65, N211, N85, T86, R89, A178, P179 and 5206 wherein the substitutions are different from Y60A/F, T61A/G, A62G/S, D63T/R, S66A, F90A/R/Y and Y92A or at least one amino acid substitution selected from G53L, A121R/W and V170I, wherein the positions are numbered by reference to the amino acid sequence set forth in SEQ ID NO: 1.

3. The esterase variant according to claim 1, wherein said esterase comprises at least one amino acid substitution at a position selected from the group consisting of Y60, T61, D63, S66, F90, Y92, F208, T157, T176, S65 and N211, wherein the substitutions are different from Y60A/F, T61A/G, D63T/R, S66A, F90A/R/Y and Y92A or at least one amino acid substitution selected from G53L, A121R/W and V170I, wherein the positions are numbered by reference to the amino acid sequence set forth in SEQ ID NO: 1.

4. The esterase variant according to claim 1, wherein said esterase comprises at least one substitution selected from the group consisting of Y60M, T61M/V, D63N/Q, S66H, F90W, Y92G/N/P/Q/T, F208I/L/W/G/S/N/A/R/T, T157E/QN/G, T176H/N/Q, S65T, G53L, A121R/W, V170I and N211Q, wherein the positions are numbered by reference to the amino acid sequence set forth in SEQ ID NO: 1.

5. The esterase variant according to claim 1, which has at least two substitutions at positions selected from G53, P58, G59, Y60, T61, A62, D63, A64, S65, S66, L67, A68, N85, T86, R89, F90, D91, Y92, P93, R96, A121, G128, H129, M131, G132, G133, G134, L152, T153, P154, W155, H156, T157, V170, T176, V177, A178, H183, 5206, F208, A209, P210, S223 and N211, wherein the positions are numbered by reference to the amino acid sequence set forth in SEQ ID NO: 1.

6. The esterase variant according to claim 5, wherein said esterase comprises at least two substitutions at positions selected from Y60, T61, A62, D63, A64, S66, A68, N85, R89, F90, Y92, H129, W155, T176, V177, S206, F208 and N211, wherein the positions are numbered by reference to the amino acid sequence set forth in SEQ ID NO: 1.

7. The esterase variant according to claim 5, wherein said esterase comprises at least two substitutions at positions selected from S65, Y92, A121, T157, V170, T176, F208 and S223, wherein the positions are numbered by reference to the amino acid sequence set forth in SEQ ID NO: 1.

8. The esterase variant according to claim 1, wherein said esterase further comprises the combination of substitutions consisting in D203C+S248C, wherein the positions are numbered by reference to the amino acid sequence set forth in SEQ ID NO: 1.

9. The esterase variant according to claim 1, which comprises at least one substitution or combination of substitutions selected from the group consisting of G53L, A121R/W, V170I Y60M, T61M/V, D63N/Q, S66H, F90W, Y92G/N/P/Q/T, S65T, T157E/Q/N/G, T176H/N/Q, N211Q, F208I/L/W/G/SN/A/R/T, F208W+V170I, Y92P+F208L, Y92P+F208W, T176H+F208W, V170I+A121S, V170I+A121S+S223A, F208W+T157Q, F208W+T157N, F208W+T157S, F208W+S65T, F208W+T157E, F208W+D203C+S248C and F208I+D203C+S248C, wherein the positions are numbered by reference to the amino acid sequence set forth in SEQ ID NO: 1.

10. A nucleic acid encoding an esterase variant according to claim 1.

11. An expression cassette or vector comprising the nucleic acid of claim 10.

12. A host cell comprising the nucleic acid of claim 10.

13. A composition comprising an esterase variant according to claim 1.

14. A method of producing an esterase comprising:
(a) culturing the host cell according to claim 12 under conditions suitable to express the nucleic acid encoding said esterase; and
(b) recovering said esterase from the cell culture.

15. A method of degrading a plastic product containing at least one polyester comprising (a) contacting the plastic product with an esterase according to claim 1 and thereby degrading the at least one polyester.

16. The method according to claim 15, further comprising (b) recovering monomers and/or oligomers resulting from the degradation of the at least one polyester.

17. The method according to claim 15, wherein the plastic product comprises at least one polyester selected from polyethylene terephthalate (PET), polytrimethylene terephthalate (PTT), polybutylene terephthalate (PBT), polyethylene isosorbide terephthalate (PEIT), polylactic acid (PLA), polyhydroxy alkanoate (PHA), polybutylene succinate (PBS), polybutylene succinate adipate (PBSA), polybutylene adipate terephthalate (PBAT), polyethylene furanoate (PEF), Polycaprolactone (PCL), poly(ethylene adipate) (PEA), polyethylene naphthalate (PEN) and blends/mixtures of these materials.

18. A polyester containing material comprising an esterase variant according to claim 1 and/or a host expressing said esterase variant.

19. A plastic compound comprising at least one polyester and an esterase variant according to claim 1 and/or a host cell expressing said esterase variant.

* * * * *

UNITED STATES PATENT AND TRADEMARK OFFICE
CERTIFICATE OF CORRECTION

PATENT NO. : 11,072,784 B2  
APPLICATION NO. : 16/819222  
DATED : July 27, 2021  
INVENTOR(S) : Vincent Tournier et al.

Page 1 of 1

It is certified that error appears in the above-identified patent and that said Letters Patent is hereby corrected as shown below:

In the Specification

Column 16,
Line 50, "3-D-1" should read --β-D-1--.

Column 17,
Line 27, "in mol of" should read --in µmol of--.
Lines 56-57, "5 m, equipped" should read --5 µm, equipped--.

In the Claims

Column 21,
Line 59, Claim 2, "and 5206" should read --and S206--.

Column 22,
Line 49, Claim 4, "T157E/QN/G," should read --T157E/Q/N/G,--.
Line 58, Claim 5, "5206," should read --S206,--.

Column 23,
Line 17, Claim 9, "F208I/L/W/G/SN/A/R/T," should read --F208I/L/W/G/S/N/A/R/T,--.

Signed and Sealed this  
Sixteenth Day of November, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 1

<210> SEQ ID NO 1
<211> LENGTH: 258
<212> TYPE: PRT
<213> ORGANISM: artificial sequence
<220> FEATURE:
<223> OTHER INFORMATION: esterase

<400> SEQUENCE: 1

Ser Asn Pro Tyr Gln Arg Gly Pro Asn Pro Thr Arg Ser Ala Leu Thr
1               5                   10                  15

Ala Asp Gly Pro Phe Ser Val Ala Thr Tyr Thr Val Ser Arg Leu Ser
            20                  25                  30

```
Val Ser Gly Phe Gly Gly Val Ile Tyr Tyr Pro Thr Gly Thr Ser
        35              40              45

Leu Thr Phe Gly Gly Ile Ala Met Ser Pro Gly Tyr Thr Ala Asp Ala
    50              55              60

Ser Ser Leu Ala Trp Leu Gly Arg Arg Leu Ala Ser His Gly Phe Val
65          70              75              80

Val Leu Val Ile Asn Thr Asn Ser Arg Phe Asp Tyr Pro Asp Ser Arg
            85              90              95

Ala Ser Gln Leu Ser Ala Ala Leu Asn Tyr Leu Arg Thr Ser Ser Pro
        100             105             110

Ser Ala Val Arg Ala Arg Leu Asp Ala Asn Arg Leu Ala Val Ala Gly
        115             120             125

His Ser Met Gly Gly Gly Thr Leu Arg Ile Ala Glu Gln Asn Pro
        130             135             140

Ser Leu Lys Ala Ala Val Pro Leu Thr Pro Trp His Thr Asp Lys Thr
145             150             155             160

Phe Asn Thr Ser Val Pro Val Leu Ile Val Gly Ala Glu Ala Asp Thr
            165             170             175

Val Ala Pro Val Ser Gln His Ala Ile Pro Phe Tyr Gln Asn Leu Pro
            180             185             190

Ser Thr Thr Pro Lys Val Tyr Val Glu Leu Asp Asn Ala Ser His Phe
        195             200             205

Ala Pro Asn Ser Asn Asn Ala Ala Ile Ser Val Tyr Thr Ile Ser Trp
        210             215             220

Met Lys Leu Trp Val Asp Asn Asp Thr Arg Tyr Arg Gln Phe Leu Cys
225             230             235             240

Asn Val Asn Asp Pro Ala Leu Ser Asp Phe Arg Thr Asn Asn Arg His
            245             250             255

Cys Gln
```